(12) United States Patent  (10) Patent No.: US 7,913,574 B2
Cain  (45) Date of Patent: Mar. 29, 2011

(54) UNIVERSAL SPHERICAL TENSION ADAPTER

(75) Inventor: Arthur L. Cain, Grove City, PA (US)

(73) Assignee: Illinois Tool Works Inc, Glenview, IL (US)

( * ) Notice: Subject to any disclaimer, the term of this patent is extended or adjusted under 35 U.S.C. 154(b) by 0 days.

(21) Appl. No.: 12/405,611

(22) Filed: Mar. 17, 2009

(65) Prior Publication Data

US 2009/0235756 A1 Sep. 24, 2009

Related U.S. Application Data

(60) Provisional application No. 61/069,816, filed on Mar. 18, 2008.

(51) Int. Cl.
*G01N 3/02* (2006.01)
(52) U.S. Cl. .......................................................... 73/856
(58) Field of Classification Search .................... 73/856; 128/87; 124/44.5
See application file for complete search history.

(56) References Cited

U.S. PATENT DOCUMENTS

| | | | | |
|---|---|---|---|---|
| 4,300,407 A | * | 11/1981 | Kopf | 74/493 |
| 4,945,902 A | * | 8/1990 | Dorer et al. | 602/38 |
| 5,722,381 A | * | 3/1998 | Mizek | 124/44.5 |
| 5,989,419 A | * | 11/1999 | Dudley et al. | 210/167.14 |

* cited by examiner

*Primary Examiner* — Jewel Thompson
(74) *Attorney, Agent, or Firm* — Day Pitney LLP

(57) ABSTRACT

A tension adapter is disclosed for a materials testing machine. The tension adapter includes a shank and a sleeve. The shank includes an enlarged head with a machined convex spherical bearing surface which forms a ring around the periphery adjacent to one end of the shaft. The opening of the sleeve includes a machine concave spherical bearing surface around the periphery thereof to form a seat for the convex spherical bearing surface. The sleeve further includes inner walls which are conical in order to allow the shank to rotate or pivot from the vertical orientation about the pivot point formed by the spherical bearing surfaces. The rotation or pivoting of the shank allows the tension adapter to align so that only tension forces are applied during materials testing.

20 Claims, 6 Drawing Sheets

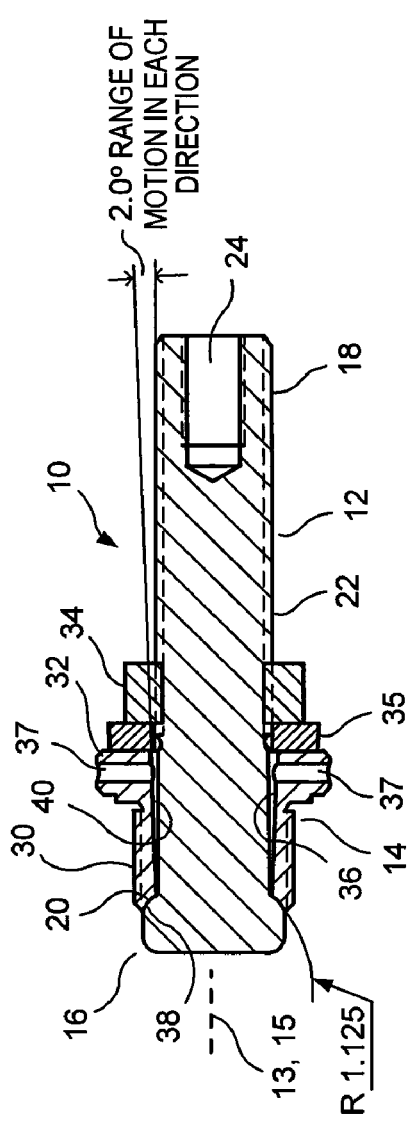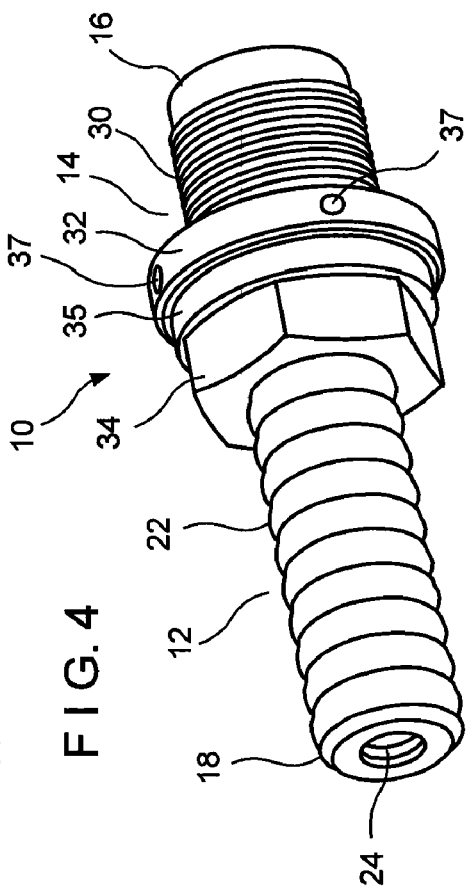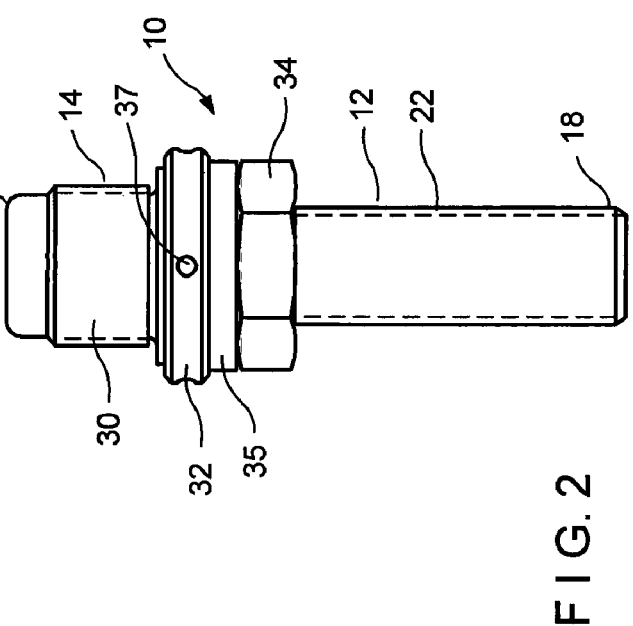

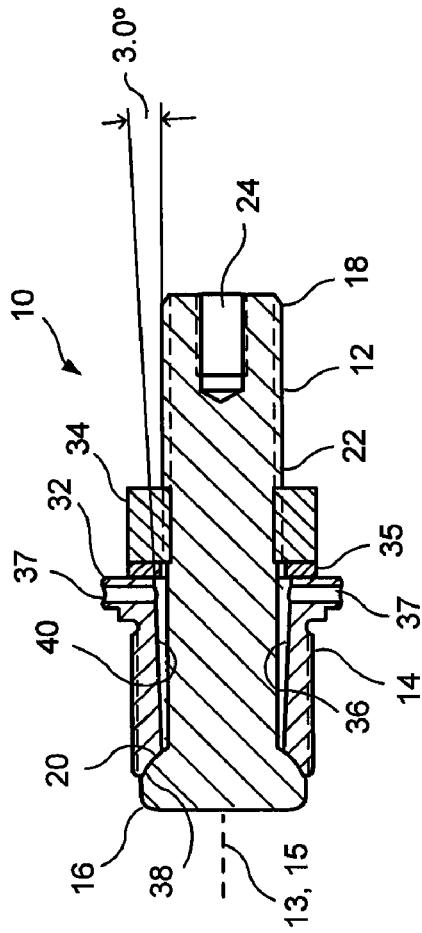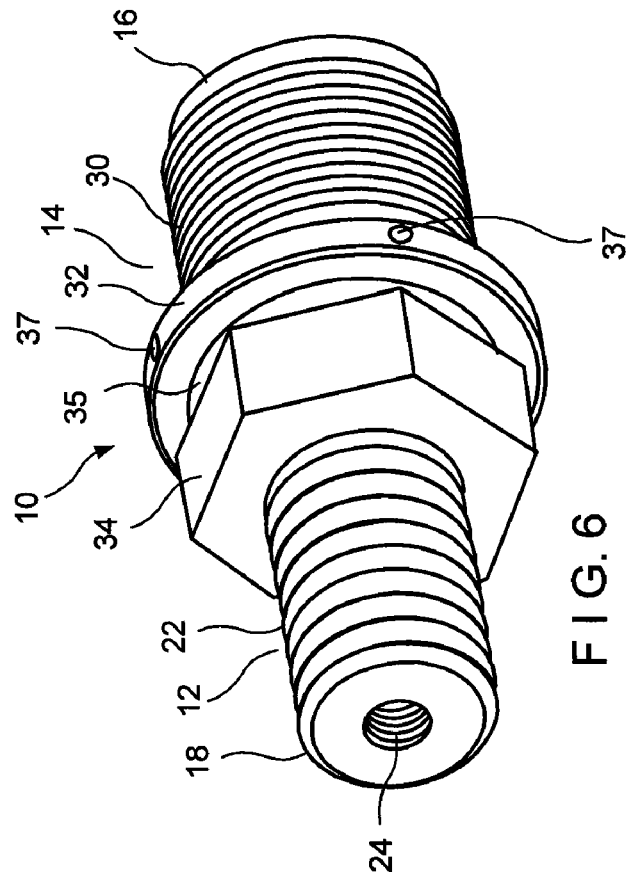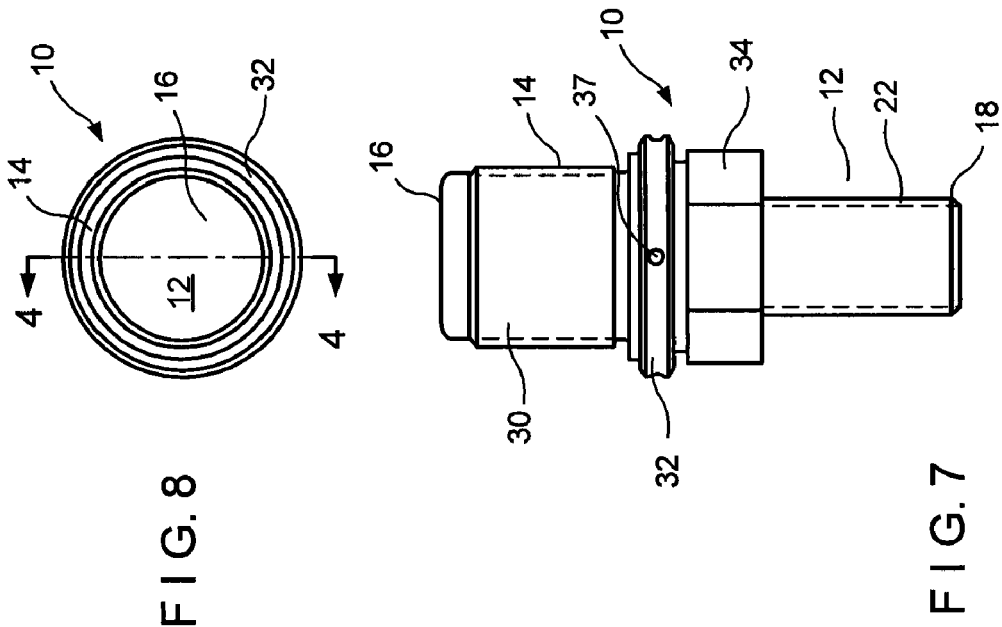

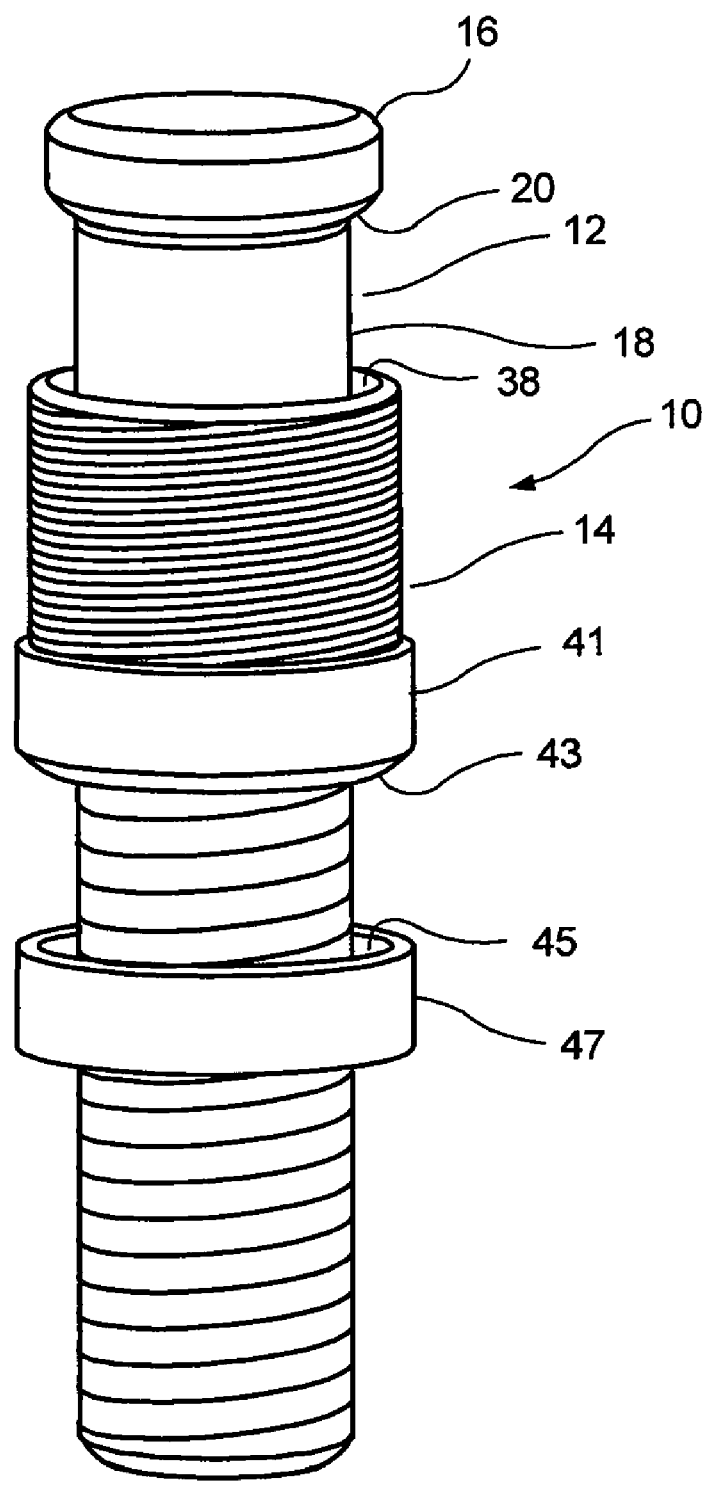
F I G. 13

UNIVERSAL SPHERICAL TENSION ADAPTER

This application claims priority under 35 U.S.C. §119(e) of provisional patent application Ser. No. 61/069,816, filed on Mar. 18, 2008, the contents of which are hereby incorporated by reference.

BACKGROUND OF THE INVENTION

1. Field of the Invention

The present invention pertains to a device for attaching tension test accessories to test machine frames in materials testing. A spherical seat inside of the device allows the test accessories to self-align as the test commences in order to assure that only tension force is applied during the test.

2. Description of the Prior Art

The prior art has included tension rods for material testing machines which use a long section of threaded rod inserted through the grip pocket of a test machine crosshead. On the side of the crosshead facing away from the tension test space, a plate is attached using fasteners. This plate is machined to accept the lower half of a spherical washer assembly. The upper half of the spherical washer sits against the lower half and the whole assembly is held together by a nut on either side of the test machine crosshead. However, tension rods that mount inside of the grip pocket require that the machine have grips enclosed inside of the crosshead. Such machines are typically dual test space machines, which offer a separate test space for tension and for compression and tend to be large and expensive. Many single test space machines are unable to use in-head tension rods. Additionally, installing the tension rods requires that the grip jaws and related parts are removed, which is a sensitive process requiring a specific method of lubrication during reinstallation. The multiple components make the device complicated, expensive and labor-intensive to install and adjust. Additionally, the multiple parts of the spherical washer and tension rod require many high precision concentric surfaces to be machined, adding uncertainty to the concentricity of the assembly.

The prior art has likewise included threaded spherical tension couplings having a protruding male threaded section intended for the test machine and a female threaded section intended to duplicate the threaded interface of the test machine. The coupling has a cylindrical section between each end inside of which the spherical seat is located, placing it well within the test space. Such an externally seated, male-female spherical coupling has the primary disadvantage of placing the spherical seat inside of the test space, which is undesirable for best tension test results and in that it consumes test space. Additionally, such couplings have typically had a large spherical radius (or radius of curvature) which resulted in significant resistance to self-alignment.

The prior art, in order to provide tension rods for a test machine already fitted with wedge grips, has further included a spherically seated tension rod device that is held in the grip jaws, similarly to the way in which the grip jaws would grip a specimen. The section held within the grip jaws is solid, and the spherical seat is contained within a cylindrical section located within the test space. From this point, the tension rod protrudes further into the test space. However, this configuration is disadvantageous in that it requires a constant grip force to stay in place. During machine testing, this requires machine power and adds an element of uncertainty to the test results. When a test machine is powered down, the grips may loosen and allow the tension rod assembly to fall out, creating a safety hazard that must be prevented by adding a retainer plate underneath. This plate must then be removed along with the tension rods. Moreover, these tension rods are used on test machines that already have a limited test space due to the grips. A spherical seat extending even further into the test space has made these unfeasible for many applications.

OBJECTS AND SUMMARY OF THE INVENTION

It is therefore an object of the present invention to provide a spherical tension alignment device for materials testing device which can be easily adapted to standard materials testing devices.

It is therefore a further object of the present invention to provide a spherical tension alignment device wherein the spherical seat is positioned generally away from the test space.

It is therefore a still further object of the present invention to provide a spherical tension alignment device with reduced resistance during alignment.

It is therefore a still further object of the present invention to provide a spherical tension alignment device which is simple to use and maintain, with a reasonable cost of production.

These and other advantages are attained by a spherical tension alignment device which includes a shank and a sleeve. The shank includes a first end with male threaded section of a typical tension rod, as well as a threaded female aperture to adapt to a larger variety of test accessories. The shank further includes a second end which is somewhat wider than the first end and includes a machined convex spherical bearing surface. The surface of the shank which is surrounded by the sleeve, immediately adjacent to the first end, is turned down to a diameter to allow a range of freedom between the shank and sleeve, expressed in degrees of rotation from the vertical (i.e., parallel to the longitudinal axis of the spherical tension alignment device).

The sleeve, which fits outwardly concentrically from the shank, includes a male threaded section for mounting onto the load cell of the materials testing machine, and a concave spherical bearing surface with a radius of curvature equal to that of the convex spherical bearing surface of the shank. Therefore, the concave spherical bearing surface serves as a seat for the convex spherical bearing surface. The center opening through which the shank is inserted is at its smallest diameter only slightly larger than the male thread of the shank. The center opening of the shank is further conical in order to optimize the strength of the part and to further allow the range of freedom of rotation between the shank and the sleeve. A washer and nut are used to maintain the sleeve in concentrically outward relationship with the shank.

DESCRIPTION OF THE DRAWINGS

Further objects and advantages of the invention will become apparent from the following description and claims, and from the accompanying drawings, wherein:

FIG. 1 is a perspective view of a first embodiment of the present invention.

FIG. 2 is a side plan view of a first embodiment of the present invention.

FIG. 3 is a top plan of a first embodiment of the present invention.

FIG. 4 is a cross-sectional view along plane 4-4 of FIG. 3.

FIG. 6 is a perspective view of a second embodiment of the present invention.

FIG. 7 is a side plan view of a second embodiment of the present invention.

FIG. 8 is a top plan of a second embodiment of the present invention.

FIG. 9 is a cross-sectional view along plane 9-9 of FIG. 8.

FIG. 13 is a further alternative embodiment of the present invention.

DETAILED DESCRIPTION OF THE PREFERRED EMBODIMENT

Figure 5:
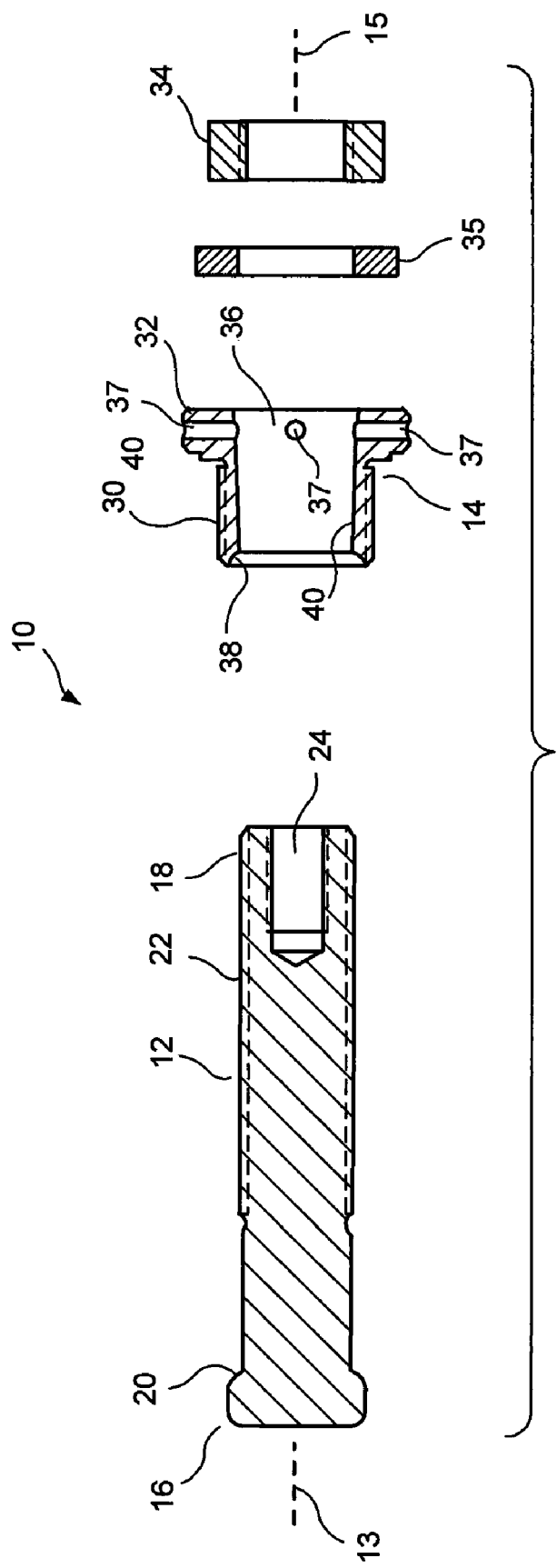
FIG. 5 is an exploded cross-sectional view along plane 4-4 of FIG. 3.
Figure 10:
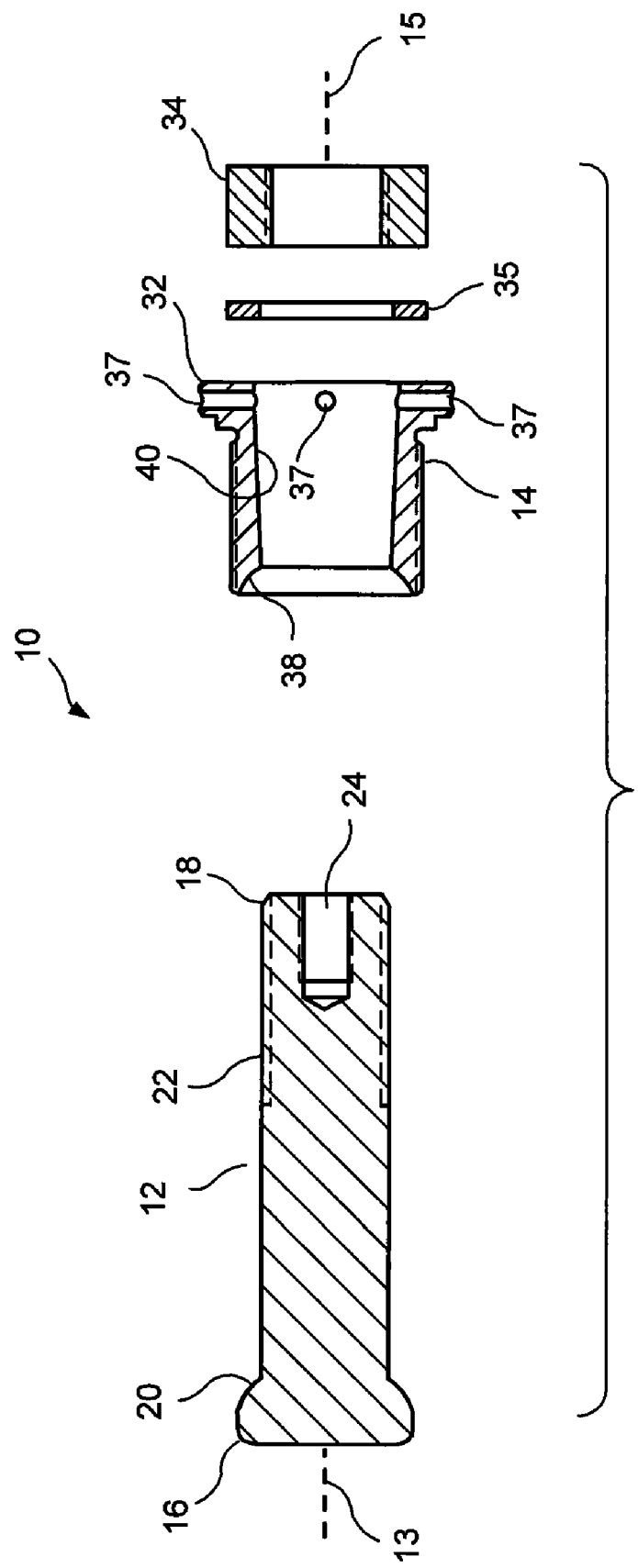
FIG. 10 is an exploded cross-sectional view along plane 9-9 of FIG. 8.
Figure 11:
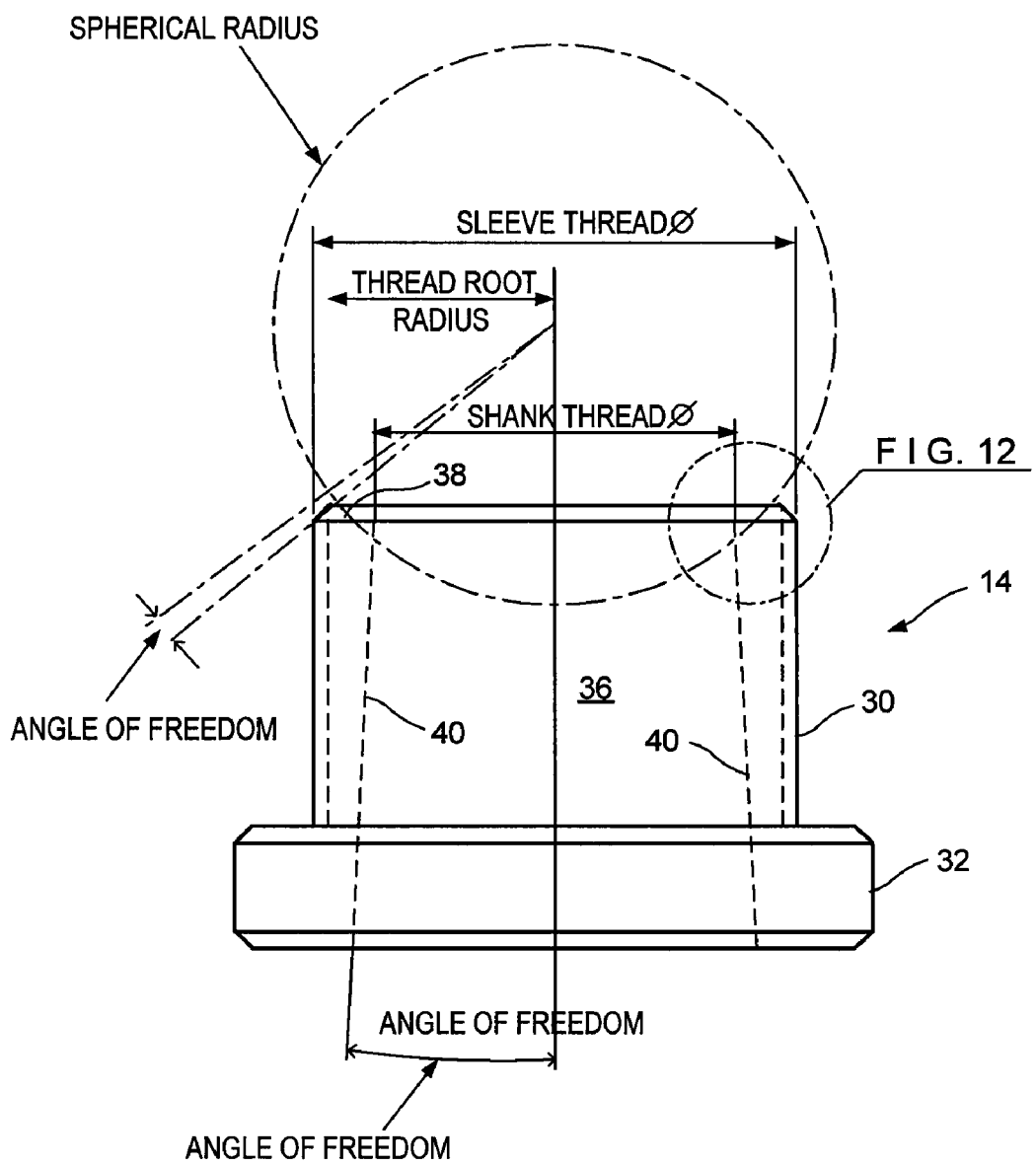
FIG. 11 is a plan view, partially in phantom, of the sleeve of an embodiment of the present invention.
Figure 12:
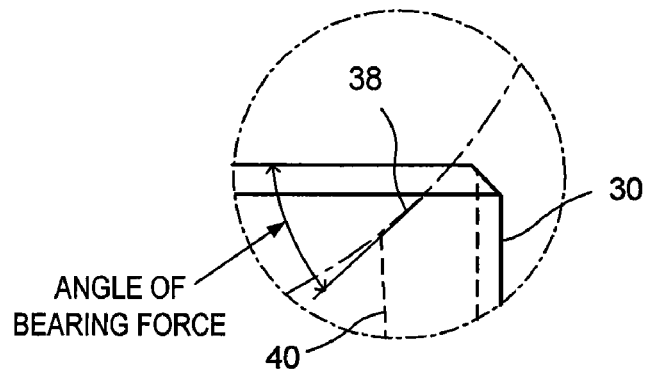
FIG. 12 is a plan view, partially in phantom, of the area of detail indicated in FIG. 11.

Referring now to the drawings in detail wherein like numerals indicate like elements throughout the several views, one sees that a first embodiment of the tension adapter 10 of the present invention is illustrated in FIGS. 1-5 while a second embodiment of the tension adapter 10 of the present invention is illustrated in FIGS. 6-10. FIGS. 11 and 12 relate to the upper portion of the sleeve of the tension adapter and are applicable to both embodiments. The first embodiment is generally directed to a universal spherical tension adapter with a 300 kN capacity, while the second embodiment is generally directed to a universal spherical tension adapter with a 600 kN capacity. However, those skilled in the art, after review of the present disclosure, will recognize that a wide range of capacities may be achieved using the principles of the present disclosure. Likewise, the tension adapter 10 is typically machined from high-strength heat-treated steel or a similar metal.

FIGS. 1 and 6 show perspective views of the first and second embodiments of the tension adapter 10. Tension adapter 10 includes shank 12 formed about longitudinal axis 13 and sleeve 14 formed about longitudinal axis 15. As further shown in FIGS. 2, 3, 7 and 8, shank 12 includes enlarged head 16 and shaft 18. The underside of head 16 includes a machined convex spherical bearing surface 20 which forms a ring around the periphery adjacent to one end of the shaft 18. The term "spherical" in this context means containing portions of a spherical surface, without the necessity of a full sphere. Shaft 18 is generally cylindrical with external male threaded portion 22 on a lower exposed portion thereof for engagement to tension accessories (not shown), as well as an internally threaded blind aperture 24 (in order to provide the capability for engagement with a wide range of tension accessories 'not shown'), formed on the lower end of the shaft 18 around a portion of the longitudinal axis 13 of the shank 12. Alternatively, a pin and clevis attachment (not shown) be used to engage the tension accessories.

Sleeve 14 includes an upper externally threaded portion 30 (typically for mounting tension adapter 10 on the load cell of the test machine 'not shown') adjacent to the upper end of sleeve 14, a cylindrical stop portion or disk 32 with radially-oriented tool-receiving apertures 37 (for use with a spanner wrench, "tommy bar" or similar tool). A central passageway 36 passes through sleeve 14. The upper edge or upper end of sleeve 14 includes a concave spherical ring-shaped edge 38 acting as a seat for the convex spherical bearing surface 20 of shank 12. The concave spherical ring-shaped edge 38 typically has substantially the same radius of curvature as the convex spherical bearing surface 20. Typically, nut 34 is threadedly engaged upon external male threaded portion 22 of shaft 18 in order to maintain washer 35 (typically made of a flexible polymer) and sleeve 14 in concentrically outward engagement around shaft 18. Washer 35 functions to absorb the impact of the shank 12 when the test specimen breaks, which typically sends a recoil force through the load train. While not illustrated, nut 34 may include tool-receiving apertures similar to the apertures 37 on cylindrical stop portion or disk 32. Similarly, as illustrated in FIG. 13, as a substitute for washer 35, a second concentric spherical seat may formed between a first ring 41 abutting the lower end of the sleeve 14, including a convex spherical surface 43 at a lower end thereof. Convex spherical surface 43 seats within a concave spherical surface 45 formed on an upper end of second ring 47 threaded around the shaft 18.

As shown best in FIGS. 11 and 12, the interior walls 40 of the central passageway 36 are inclined forming a partially conical shape. This optimizes the strength of the sleeve 14 and further provides the freedom or clearance for the shank 12 to rotate or pivot within a range (typically, but not limited to, 2 to 3 degrees deviation in either direction between longitudinal axis 13 of shank 12 and longitudinal axis 15 of sleeve 14) about the spherical seat formed by the seating of convex spherical bearing surface 20 into concave spherical ring-shaped edge 38 in response to the forces incurred on tension adapter 10 during materials testing. As shown in FIG. 4, interior walls 40 are inclined two degrees from the sleeve longitudinal axis 15 thereby allowing the embodiment of FIGS. 1-5 a deviation of up to two degrees between longitudinal axes 13, 15. Likewise, as shown in FIG. 9, interior walls 40 are inclined three degrees from the sleeve longitudinal axis thereby allowing the embodiment of FIGS. 6-10 a deviation of up to three degrees between longitudinal axes 13, 15. Furthermore, the opening formed within concave spherical ring-shaped edge 38 is only slightly larger than the diameter of external male threaded portion 22 thereby providing a maximum area of contact between convex spherical bearing surface 20 and concave spherical ring-shaped edge 38 in order to minimize compression stress and to afford the sleeve 14 as much thickness as possible to resist radial force that may have a tendency to split sleeve 14 under high load.

To use the tension device 10, the user insets shaft 18 of shank 12 into sleeve 14 and engages convex spherical bearing surface 20 into concave spherical ring-shaped edge 38. The upper externally threaded portion 30 of sleeve 14 is threaded to the load cell of the testing device (not shown) and external male threaded portion 22 or internally threaded blind aperture 24 of shank 12 is threaded to the tension accessory (not shown). The materials testing is then performed. During materials testing, the spherical seat formed by the seating of convex spherical bearing surface 20 into concave spherical ring-shaped edge 38 as well as the partially conical shape of central passageway 36, allows the shank 12 to pivot or rotate within a range, typically, but not limited to, 2 or 3 degrees of deviation in either direction between longitudinal axis 13 of shank 12 and longitudinal axis 15 of sleeve 14, in response to the forces of materials testing, thereby maintaining the desired alignment and assuring that only tension force is applied, via the shank 12, during the test.

Thus the several aforementioned objects and advantages are most effectively attained. Although preferred embodiments of the invention have been disclosed and described in detail herein, it should be understood that this invention is in no sense limited thereby and its scope is to be determined by that of the appended claims.

What is claimed is:

1. A tension adapter for materials testing including:
a shank including a shaft and an enlarged portion, the shaft including a shaft portion for engaging a tension accessory;
a sleeve with a first end and a second end, the sleeve fitting outwardly concentric from the shaft of the shank, the first end of the sleeve engaging the enlarged portion thereby forming a pivot point for the shank to pivot with respect to the sleeve.

2. The tension adapter of claim 1 whereby the shank pivots with respect to the sleeve in response to a longitudinal force on the shank, whereby the shank aligns so that only tension force is applied by the shank.

3. The tension adapter of claim 2 wherein the enlarged portion is an enlarged head.

4. The tension adapter of claim 3 wherein the enlarged head includes a convex spherical portion on an underside thereof.

5. The tension adapter of claim 4 wherein the first end of the sleeve includes an edge which further includes a concave spherical portion for engaging the convex spherical portion of the enlarged head thereby forming the pivot point for the shank to pivot with respect to the sleeve.

6. The tension adapter of claim 5 wherein a radius of curvature of the convex spherical portion is equal to a radius of curvature for the concave spherical portion.

7. The tension adapter of claim 4 wherein the sleeve includes inner walls which are at least partially conical in order to accommodate pivoting of the shank with respect to the sleeve.

8. The tension adapter of claim 7 wherein the shank includes a shank longitudinal axis, the sleeve includes a sleeve longitudinal axis, and the inner walls are inclined to accommodate a range of pivoting of the shank wherein the shank longitudinal axis may deviate up to two degrees from the sleeve longitudinal axis.

9. The tension adapter of claim 7 wherein the shank includes a shank longitudinal axis, the sleeve includes a sleeve longitudinal axis, and the inner walls are inclined to accommodate a range of pivoting of the shank wherein the shank longitudinal axis may deviate up to three degrees from the sleeve longitudinal axis.

10. The tension adapter of claim 4 wherein the sleeve includes a sleeve threaded portion for engaging a load cell of a test machine.

11. The tension adapter of claim 10 wherein the sleeve threaded portion is a first externally threaded portion.

12. The tension adapter of claim 11 wherein the first externally threaded portion is adjacent to the first end of the sleeve.

13. The tension adapter of claim 10 wherein the sleeve includes a cylindrical stop portion adjacent to the sleeve threaded portion.

14. The tension adapter of claim 13 wherein the cylindrical stop portion includes tool-engaging elements.

15. The tension adapter of claim 14 wherein the tool-engaging elements are radially oriented apertures.

16. The tension adapter of claim 11 wherein the shaft portion for engaging a tension accessory is threaded.

17. The tension adapter of claim 16 wherein the shaft portion is a second externally threaded portion.

18. The tension adapter of claim 17 further including a nut engaging the second externally threaded portion and abutting the sleeve thereby retaining the sleeve in outwardly concentric relation with the shaft.

19. The tension adapter of claim 17 wherein the shaft further includes an internally threaded aperture for engaging a tension accessory.

20. The tension adapter of claim 1 wherein the sleeve and the shank are formed of machined metal.

* * * * *